United States Patent [19]

Keys

[11] Patent Number: 5,686,023
[45] Date of Patent: Nov. 11, 1997

[54] $C_7$-$C_{12}$ DIOL AND DIOL ALKOXYLATES AS COUPLING AGENTS FOR SURFACTANT FORMULATIONS

[75] Inventor: Robert O. Keys, Columbus, Ohio

[73] Assignee: Witco Corporation, Greenwich, Conn.

[21] Appl. No.: 430,516

[22] Filed: Apr. 27, 1995

[51] Int. Cl.$^6$ .............................. B01F 17/42; B01J 13/02; C11D 3/20
[52] U.S. Cl. .................. 252/351; 252/312; 252/357; 510/506; 510/525
[58] Field of Search ..................... 252/312, 351, 252/DIG. 1, DIG. 14, 357; 570/525, 506

[56] References Cited

U.S. PATENT DOCUMENTS

| | | | |
|---|---|---|---|
| 2,679,482 | 5/1954 | Ross | 252/531 |
| 2,956,025 | 10/1960 | Lew | 252/559 |
| 2,997,447 | 8/1961 | Russell et al. | 252/351 |
| 3,463,735 | 8/1969 | Stonebraker et al. | 252/523 |
| 3,705,113 | 12/1972 | Sharman | 252/555 |
| 3,766,062 | 10/1973 | Wixon | 252/8.7 |
| 3,779,934 | 12/1973 | Altenschopfer et al. | 252/351 X |
| 3,819,522 | 6/1974 | Zmoda et al. | 252/170 |
| 3,956,199 | 5/1976 | Dawson et al. | 252/545 |
| 4,140,641 | 2/1979 | Ramachandran | 252/8.75 |
| 4,338,212 | 7/1982 | Wegener et al. | 252/DIG. 1 |
| 4,414,128 | 11/1983 | Goffinet | 252/111 |
| 4,454,049 | 6/1984 | MacGilp et al. | 252/8.8 |
| 4,692,277 | 9/1987 | Siklosi | 252/538 |
| 5,202,050 | 4/1993 | Culshaw et al. | 252/170 |
| 5,399,272 | 3/1995 | Swartley et al. | 252/8.8 |
| 5,427,697 | 6/1995 | Swartley | 252/8.8 |

FOREIGN PATENT DOCUMENTS

240727 A2  10/1987  European Pat. Off. .

OTHER PUBLICATIONS

"Technical Bulletin Shell Chemical Company," SC:1306–91, (1991).
Selected pages, Product Bulletin, Dowanol Glycol Ethers, Dow Chemical Company, (1991).

*Primary Examiner*—Richard D. Lovering
*Attorney, Agent, or Firm*—Scully, Scott, Murphy & Presser

[57] ABSTRACT

Disclosed are stable monophasic liquid compositions comprising water, one or more cationic, anionic, amphoteric and/or nonionic surfactants, exhibiting partial solubility in water or in concentrated formulations, and one or more coupling agents which are $C_7$-$C_{12}$ alkane substituted with two hydroxyl groups or alkoxylates thereof with up to 20 moles of one or more of ethylene oxide, propylene oxide and/or butylene oxide.

10 Claims, No Drawings

$C_7$-$C_{12}$ DIOL AND DIOL ALKOXYLATES AS COUPLING AGENTS FOR SURFACTANT FORMULATIONS

BACKGROUND OF THE INVENTION

The present invention relates to aqueous compositions containing solubilized or dispersed therein one or more useful surfactants which exhibit low solubility (or no solubility at all) in water, especially in the presence of electrolytes and/or pH agents. For purposes of this application, a substance is considered to be "solubilized" in water if the material is dissolved in the water or if it is uniformly dispersed or distributed therein, or emulsified therein, so as to exhibit the physical appearance and physical properties of a single-phase system (whether as an emulsion, an organic-based formula, or a water-based formula).

As is well known, surfactants can be used to perform a wide variety of useful purposes, ranging from cleaning and surface protection through deposition of coatings, fabric softening, foam stabilization, oil recovery, ore flotation, asphalt emulsification, achieving or enhancing rewetting effectiveness and penetrating power, and a large variety of other capabilities set forth hereinbelow. However, in many cases the ability to take advantage of such surfactants' useful properties is limited by the low solubility and/or dispersibility of many surfactants and surfactant blends in water.

There is also need in the marketplace for products with higher levels of concentration of surfactants or active ingredients, thus minimizing the amounts of water in the products. As the amount of water in the formulations is reduced, and as formulations add more (and more complex) ingredients, the fluidity and stability become more difficult to maintain. Often the surfactants become insoluble gels when diluted in water, or become hazy or even split into different phases. Surfactants often become insoluble in formulations where the concentration of inorganic salts is very high. In other surfactant formulations, maintaining the fluidity and dispersibility of the surfactant in water are serious problems which limit their use and application. Many surfactants are difficult to even disperse in water, requiring both hot water and long periods of mixing for dissolution into solution.

Hydrotropes or, more generally, coupling agents are added to surfactant formulations to increase the amount of the relatively water-insoluble surfactants that can be solubilized into the system. In most cases, they do not act as surfactants to lower surface tension but they often allow surfactants in the presence of salts or electrolytes to be added and subsequently dispersed into water at higher concentrations or at lower viscosities of the formulation than is otherwise achieved using only surfactant and water. These coupling agents assist surfactants by increasing the surfactant's solubility in water and its stability in the formulation, especially in the presence of salts, electrolytes and/or pH agents.

Hydrotropes or coupling agents generally contain short chained ($C_2$-$C_6$) hydrophohes with more bulky hydrophilic group(s) such as hydroxyl and/or sulfonates making them completely water-soluble. They are normally added to stabilize formulations of surfactants, salts and water and to hold them in single-phase systems.

Materials that have been proposed for use as coupling agents include hexylene glycol, propylene glycol, dipropylene glycol, diethylene glycol, any of various lower alkoxy-capped glycols or polyglycols, particularly where the glycol is ethylene glycol or propylene glycol, such as ethylene glycol monobutyl ether, alcohols such as isopropanol and ethanol, and certain aryl sulfonates such as sodium naphthalene sulfonate and sodium xylene sulfonate, as well as some phosphate esters. However, despite the abilities of these water-soluble products as coupling agents that have been suggested for these materials, there remains a need and an interest in identifying coupling agents and systems containing such coupling agents which not only exhibit superior stability and superior ability to solubilize relatively water-insoluble agents but also improve formulation fluidity, dispersiblity and product performance.

In addition, coupling agents that have improved permissible-exposure limits, higher flash points (over, for instance, isopropanol and ethanol), and lower odor (compared to, for example, butyl CELLOSOLVE or isopropanol) would have substantial importance to formulations and consumers. Other coupling agents such as sodium xylene sulfonate containing aromatic rings have come under environmental scrutiny in recent times.

The composition disclosed in U.S. Pat. No. 4,692,277 represents an attempt to incorporate certain diol solvents into hard surface cleaning formulations. The disclosure, however, is limited to liquid hard surface detergents/cleaners which contain at most 10% of a surfactant, and which must contain 1% to 30% of a detergency builder salt. The necessity of these components in the indicated amounts attests to the specific, limited nature of the teachings of this patent. More fundamentally, the disclosure of this patent was concerned solely with the solvent power of $C_6$-$C_{16}$ diols as to their effect on soap scum removal when combined with both surfactants and salt builders, and completely fails to suggest or appreciate that it is possible, through selection of components according to the present invention, to employ certain diols and/or alkoxylates thereof so as to attain the solubilization of much higher amounts of less soluble surfactant(s) while retaining the desired monophasic state of the resulting composition. Thus, in turn, this patent thereby also fails to suggest any of the many end-use (especially monophasic) formulations that can be prepared embodying the compositions afforded by the present invention in combination with other hydrophobic surfactants, be they active ingredients or otherwise.

BRIEF SUMMARY OF THE INVENTION

One aspect of the present invention resides in a stable monophasic liquid composition characterized by the ability to solubilize increased amounts of surfactant into said composition while retaining an essentially monophasic state, which composition is useful as a dispersant of hydrophobic material and as a foam stabilizer, consisting essentially of water;

one or more surfactants selected from the group consisting of cationic surfactants, anionic surfactants, amphoteric surfactants, and nonionic surfactants, and mixtures thereof; and one or more coupling agents selected from the group consisting of straight, branched and cyclic, saturated, alkanes containing 7 to 12 carbon atoms and substituted with two hydroxyl groups, and alkoxylates thereof with up to 20 moles of ethylene oxide, propylene oxide, butylene oxide, and/or random or block mixtures thereof, in an amount effective to increase the amount of said one or more surfactants that can be solubilized in said monophasic liquid composition.

Another aspect of the invention is the method of increasing the amount of cationic, anionic, amphoteric, or nonionic surfactant or a mixture of two or more thereof that can be solubilized in water, especially as to surfactants which exhibit low solubility in water, the method consisting of solubilizing together water, one or more of said surfactants, and one or more coupling agents selected from the group consisting of straight, branched and cyclic, saturated, alkanes containing 7 to 12 carbon atoms and substituted with two hydroxyl groups, and alkoxylates thereof with up to 20 moles of ethylene oxide, propylene oxide, butylene oxide, or mixtures thereof, in an amount effective to increase the amount of said surfactant that can be solubilized in the resulting aqueous composition.

DETAILED DESCRIPTION OF THE INVENTION

The present discovery has particular utility with surfactants that are either insoluble in water, or exhibit partial solubility in water such as up to 10 grams per 100 milliliters of water (in the absence of surfactants, coupling agents, or other solubility-enhancing additives). However, the present discovery also is useful with surfactants which exhibit even complete solubilities in water but which are difficult to disperse or to produce fluid, low viscosity formulations in water, and/or highly concentrated surfactant blends with or without electrolytes, builders and/or pH agents or other active agents.

Satisfactory surfactants useful herein can readily be identified in well-known sources such as McCutcheon's Detergents & Emulsifiers, and the CTFA Cosmetic Ingredient Dictionary.

Anionic surfactants include in particular organosulfonates and organosulfates, which can be characterized by the formula $X^1-A^1$ wherein $A^1$ denotes sulfonate or sulfate, attached anywhere to $X^1$ and most often at one end of $X^1$, and $X^1$ denotes:

alkyl containing 6 to 40 carbon atoms, optionally substituted with 1 to 10 hydroxyl groups, and optionally substituted with aryl (particularly phenyl) which is optionally substituted with one or more alkyl or alkylene groups containing 1 to 20 carbon atoms and up to 3 carbon-carbon double bonds;

alkylene containing 6 to 40 carbon atoms and 1 to 6 carbon-carbon bonds, and optionally substituted with 1 to 10 hydroxyl groups, and optionally substituted with aryl (particularly phenyl) which is optionally substituted with one or more alkyl or alkylene groups containing 1 to 20 carbon atoms and up to 3 carbon-carbon double bonds;

amides and esters containing a total of 6 to 50 carbon atoms and optionally containing 1 to 6 carbon-carbon double bonds;

polyalkoxy segments, particularly homopolymers, random copolymers, and block copolymers, of ethylene oxide and/or propylene oxide, containing 2 to 200 alkoxy units, per se or terminated with alkyl or alkylene containing 2 to 40 carbon atoms, which may optionally be substituted with 1–10 hydroxyl groups, or terminated with aryl (particularly phenyl) which may optionally be substituted with one or more alkyl or alkylene groups containing 1 to 20 carbon atoms and up to 3 carbon-carbon double bonds.

The anionic component is counterbalanced by a cation X which is preferably an alkali metal (e.g. sodium, potassium or lithium).

Cationic surfactants include quaternary ammonium compounds, particularly those of the formula $$(Q^1)(Q^2)N^+(Q^3)(Q^4)—(An)^-$$

wherein $(An)^-$ is an anion such as halide (especially bromide or chloride), methylsulfate, or ethylsulfate, and $Q^1$, $Q^2$, $Q^3$ and $Q^4$ are selected such that 2 or 3 thereof are $C_{1-4}$ alkyl (optionally one of which is benzyl) and 1 or 2 thereof are alkyl or alkylene containing 8 to 24 carbon atoms and optionally up to 3 carbon-carbon double bonds, or poly (alkoxy) wherein each alkoxy unit is ethoxy or propoxy, containing up to 200 alkoxy units. Also included are polymeric quaternary ammonium salts including those known generically as polyquaternium $-1$, $-2$, $-4$, $-5$, $-6$, $-7$, $-8$, $-9$, $-10$, $-11$, $-12$, $-13$, and $-14$.

Amphoteric surfactants particularly include those of the formula (IVa) and (IVb)

$$R^4-(OC_3H_6)_{0-1}(C(O)NH(CH_2)_{1-3})_{0-1}-N(Z^1)(Z^2)_{0-1}-ZCOOH \quad (IVa)$$

$$R^4-(OC_3H_6)_{0-1}(C(O)NH(CH_2)_{1-3})_{0-1}-N(Z^1)(Z^2)_{0-1}-ZSO_3H \quad (IVb)$$

salts thereof with an alkali metal X or ammonium cation and mixtures of any said compounds and salts, wherein X is as defined above, $R^4$ is straight or branched alkyl or alkylene, or cyclic or heterocyclic aromatic which is optionally substituted with alkyl, and contains 4 to 40 carbon atoms and 0–3 carbon-carbon double bonds, $Z^1$ and $Z^2$ are independently of each other H, $C_fH_{2f+1}$ or $C_fH_{2f}OH$ wherein f is 1 to 6 and preferably 1, Z or 3 or, in formula (IVa), one of $Z^1$ and $Z^2$ can be $—ZCOOH$ or $—ZCOOX$, and Z is $(CH_2)_f$, $CH_2CH_2OCH_2$, or $CH_2CHOHCH_2$.

Formulas (IVa) and (IVb) embrace betaines, sulfobetaines (sultaines), glycinates and propionates, which are commercially available and/or can readily be synthesized. Examples of preferred amphoteric surfactants include fatty betaines such as lauryl dimethyl betaine (e.g. REWOTERIC® AM-DML-35) (this and all other REWOTERIC®-branded compounds are marketed by Witco Corp.) and N-lauryl-beta-iminopropionic acid, mono-sodium salt (e.g. REWOTERIC® AM-LP); glycinates such as N-cocoylamidoethyl-N-(2-hydroxyethyl)-N-carboxymethyl glycine, sodium salt (e.g. REWOTERIC® AM-2C-W) and as lauryl hydroxy sultaine (e.g. REWOTERIC®-AM-B-15); propionates such as sodium cocoamphopropionate (e.g. REWOTERIC® AM-KSF-40); and sulfobetaines such as lauryl hydroxy sultaine (e.g. REWOTERIC AM-CAS).

Preferred $R^4$ groups include alkyl and alkylene radicals derived from fatty acids. Other preferred $R^4$ groups include benzyl and alkyl-substituted benzyl.

Nonionic surfactants include any nonionic compounds having surface active capability. Examples include esters, amides, and alkanolamides, containing a total of 6 to 40 carbon atoms, optionally zero to 3 carbon-carbon double bonds and optionally substituted with 1 to 20 hydroxyl groups (as e.g. polyglycol) esters;

homopolymers, random copolymers and block copolymers of ethylene oxide and/or propylene oxide and/or ethylene glycol and/or propylene glycol, containing 2 to 200 repeating units;

any of the foregoing homopolymers, random copolymers and/or block copolymers, but especially poly(ethylene oxide), substituted with alkyl or alkylene containing 1 to 40 carbon atoms and optionally up to 6 carbon-carbon double bonds, and optionally 1 to 20 hydroxyl groups, or with an ester, amide, amine, alkanolamide or with an aryl group (especially phenyl) or an aryl-alkyl group, itself optionally substituted with alkyl or alkylene containing up to 40 carbon atoms and optionally containing 6 carbon-carbon double bonds; and sorbitol derivatives, including those known generically polysorbate –20, –32, –40, –60, –61, –65, –80, –81, and –85.

The particular selection of the type of emulsifier, and the particular compound selected, for any given application can readily be made by those of ordinary skill in this art with reference to the identity or identities of the intended application and the surface properties needed, with due consideration to the amount thereof and to the properties desired of the final product. In particular, the HLB (hydrophilic-lipophilic balance) which needs to be exhibited by the surfactant chosen can likewise be determined quite readily for any particular end-use application.

The critical feature of the discovery represented by the presently claimed invention is the discovery of a carefully chosen class of coupling agents which, in the overall water-based systems disclosed herein, exhibit remarkable and unforeseen properties rendering the resulting compositions superior in many respects to those previously available.

The coupling agents of choice include saturated hydrocarbons containing 7 to 12 carbon atoms and substituted with two hydroxyl groups. Preferably, one of the hydroxyl groups is on a primary carbon atom and one is on a secondary carbon atom. The agents can be straight-chained, branched-chained or cyclic. A particularly preferred coupling agent is 2,2,4-trimethyl-1,3-pentane diol (referred to herein as "TMPD"). Another preferred coupling agent is 2-ethylhexyl-1,3-diol. TMPD is a solid at room temperature whereas 2-ethylhexyl-1,3-diol is a fluid liquid at room temperature.

Another preferred category of coupling agents includes the alkoxylates formed by alkoxylating TMPD or another $C_7$–$C_{12}$ alkane diol with 1 to 20 moles of ethylene oxide, propylene oxide, butylene oxide, or any combination thereof. That is, the alkoxylate is substituted at one or both hydroxyl sites with one alkoxy moiety, or with a segment of 2 or more alkoxy units wherein each alkoxy unit is ethoxy, propoxy or butoxy. Segments can be all of one type of alkoxy group, can be composed of blocks wherein each block is composed of only one type of alkoxy group, or can be composed of varying combinations of 2 or all 3 types of alkoxy group. It is believed that such alkoxylation produces a derivative wherein a linear polyalkoxylate chain is pendant predominately from the 1-terminal oxygen atom. This alkoxylation makes these higher molecular weight diols fluid and easier to formulate.

TMPD can readily be synthesized, but is also commercially available from Eastman Chemical Company. The corresponding alkoxylates can readily be prepared in accordance with conventional industrial chemical synthetic processing, by reaction of the TMPD with the appropriate desired number of moles of ethylene oxide, propylene oxide, and/or butytene oxide.

As for the properties of TMPD and alkoxylates thereof, TMPD is a white solid at room temperature and melts at 50° C. It has a water solubility itself of about 1–2% in water at 25° C. On the other hand, the ethoxylates containing 2 to 20 moles of ethylene oxide are highly soluble in water. The ethoxylates of TMPD are clear liquids with freezing points below –10° C. Ethoxylates with 1–3 moles of ethylene oxide exhibit cloud points in water of about 30°–40° C., whereas ethoxylates with higher degrees of ethoxylation exhibit cloud points above 60° C.

The propoxylates are also clear liquids with freezing points below –10° C., and have very limited solubility in water compared to the ethoxylates. Using either ethylene oxide, propylene oxide, butylene oxide, or a selected mixture thereof on the $C_7$ to $C_{12}$ diols, one can achieve optimized solubilization and dispersibility as needed for any application.

In aqueous-based formulations corresponding to the invention described and claimed herein, the $C_7$–$C_{12}$ diols and alkoxylates thereof contribute to a number of very desirable properties which render such compositions superior to those previously known.

Compositions in accordance with the present invention exhibit superior stability, by which is meant that they do not separate into more than one phase even upon standing, without agitation, for prolonged periods of time on the order of a year or longer. They generally form more fluid formulations, require lower levels of the diol or diol alkoxylate than of other coupling agents to function, and are nonflammable with high exposure limits. They also give very easy-to-disperse formulations even when the formulations are highly concentrated, and thus function better in each application. They generally give added fluidity to even difficult to handle surfactants and enable those same surfactants to be dispersed in much colder water than is the case with other coupling agents.

The compositions of the present invention are particularly useful in applications that take advantage of their ability to disperse hydrophobic material, to stabilize foam, and to enhance the penetration and wetting exhibited by the compositions. Examples of such applications include:

Oil dispersants and oil slick dispersants, wherein one applies onto oil (for instance, onto a film of oil) a sufficient amount of a composition according to the present invention, containing a sufficient concentration of surfactant, such that the composition disperses the oil.

Oil well stimulation and oil recovery aids, wherein one injects into an oil well a composition according to the present invention in order to penetrate into the surface of the borehole and assist liberation of crude oil from the matrix material into the hole, from which it can be brought to the surface.

Vehicles for hydrophobic sheeting agents such as mineral oil and silicone oil. Such oils can readily be dispersed in Compositions, according to the present invention, and the resulting formulations are highly satisfactory when sprayed or otherwise applied to a surface (such as freshly washed automobile surfaces) to impart a lustrous, water-repellent film to the surface.

Formulation of fabric and textile softeners, wherein components capable of imparting fabric softening (typically, quaternary ammonium compounds such as di-($C_{12-22}$-alkyl)-di($C_1$–$C_4$ alkyl) ammonium chloride or methylsulfate, or 1,3-disubstituted imidazolinium salts) are incorporated into the composition thereby forming a fluid, monophasic, typically clear composition.

Paper deinking and ink flotation, wherein waste inked paper is pulped as a slurry in an aqueous liquid comprising a composition according to the present invention so that ink is liberated from the paper, and prevented from redepositing onto the paper; typically the ink is dispersed or even fully solubilized in the liquid composition of this invention or when the ink particles are floated from the fibers.

Paper debonding, wherein paper fibers are pulped in the headbox of a papermaking machine as a slurry in an aqueous liquid comprising a composition according to the present invention, just prior to feeding the slurry onto the dewatering screen, to improve the softness of the paper product formed.

Asphalt emulsions, wherein finely divided asphalt is emulsified (at loadings typically 1–20 wt. %), with or without particulate filler such as sand, in an aqueous phase which comprises the composition according to the present invention.

Hair and skin conditioning formulations, wherein effective amounts (e.g. 0.1 wt. % to 10 wt. % or more) of emollients, humectants, and/or slip and conditioning agents (e.g. organopolysiloxanes and the like) are incorporated with the composition of the present invention to create formulations that are monophasic and can be made to be translucent or even clear. Compounds suitable for use as emollients, humectants and conditioners in formulations for skin care or hair care can be found in the CTFA Cosmetic Ingredient Dictionary, 3d Edition, and in the CTFA Cosmetic Ingredient Handbook.

Corrosion inhibitors, wherein an effective amount of a hydrophobic corrosion inhibiting material (such as liquid or waxy-solid fatty ester, paraffinic hydrocarbon or silicone) is dispersed in a composition according to the present invention. The resulting formulation is applied to any surface to which one desires to apply a film that protects against corrosion.

Ore flotation, wherein a relatively hydrophobic material used as e.g. a collector or frother—depending on the characteristics of the particular separation desired in the flotation cell—is dispersed in a composition according to this invention. An amount effective to carry out the intended function is then fed (on a batch or continuous basis) to the cell. The composition of the present invention permits the formulator to improve the dispersibility of the collector(s) which are often very hydrophobic. This can often improve performance of the mineral separation by improving the efficiency of the chemical's dispersiblity. This can enable the operator to use smaller amounts (at the higher concentration of active now available) of the formulation to achieve the desired purpose.

Rinse aids, such as used in automatic dishwashers, wherein application of the composition of the present invention disperses residual hydrophobic matter, including cleaner residues and films.

Suspension concentrates and emulsifiable concentrates of herbicides, pesticides, miticides, fungicides, and/or bactericides, wherein one or more liquid or solid, generally hydrophobic, active ingredients are dispersed in a composition according to the present invention. The concentrate can be applied as is on or around desired vegetation; but is more often mixed (e.g. at the point of use) with water of dilution to form a final formulation having the desired concentration of active ingredient(s). This application takes advantage of the noteworthy property of this invention that addition of the water for dilution does not disrupt the monophasic state, nor the fluidity, of the formulation.

Generally speaking, the amount of coupling agent can range from about 0.1 wt. % or 10 wt. % to about 50 wt. %, with the particular amount readily identified by the formulator. Water may not necessarily be present, but usually is present in amounts that can be up to about 90–95 wt. %.

The one or more surfactants (which may exhibit low, solubility in water) will generally be present in amounts on the order of 0.1 wt. % to about 90 wt. %, and similarly the particular amount can readily be ascertained by the formulator. The invention is particularly utilizable in embodiments wherein the amount of surfactant(s), in the aggregrate, exceeds 10 wt. %, i.e. 15 wt. % or more. Indeed, it has quite surprisingly been determined that compositions in accordance with the present invention can be prepared wherein the amount of surfactant(s) is at least 20–25 wt. %, or even 30 wt. % or higher, ranging up to 50 wt. % or higher, yet the composition remains monophasic and retains its fluidity and its ability to be compounded with other components without suffering phase separation, turbidity or excessive viscosity.

The compositions of the present invention can also optionally contain other components, depending on the additional properties one may wish to provide in the finished composition. Such additional components include, but are not limited to, additional coupling agents and solvents, thickeners, fragrances, coloring agents, hydrocarbon actives, and so forth.

The compositions of the present invention have particular usefulness in applications not calling for the presence of inorganic or organic salts. It is customary to incorporate quantities of such salts, known often as "builder" salts or "detergency builder" salts, particularly when cleaning functionality like hard surface cleaning is desired. However, the present invention is applicable to a considerable number of utilities that do not need the presence of builder salts, since they are not related to cleaning hard surfaces. The ability of the present invention to be so versatile and functional in applications without builder salts is one of the many unexpected and noteworthy aspects of the present invention.

The following are but a few examples of more particular formulations embodying the compositions of the present invention. These examples are provided for purposed of illustration, and should not be deemed to limit the scope of the invention.

| EXAMPLES | | |
|---|---|---|
| Component | Typical Amount wt. % | Exemplary Amount (wt. %) |
| Carwash Sheeting Spray | | |
| Dicoco dimethyl ammonium chloride (78% in isopropanol) | 10–30 | 20 |
| Diol or diol alkoxylate (e.g. TMPD or TMPD-monoethoxylate) | 2–10 | 5 |
| Mineral seal oil | 20–30 | 25 |
| Water | 40–60 | 50 |
| Clear Fabric Softener | | |
| Di(soft tallow) dimethyl ammonium chloride | 30–40 | 35 |
| TMPD | 5–12 | 10 |
| CaCl$_2$ | 0.1–0.4 | 0.2 |
| Fragrance/dye preservative | trace | trace |
| Water | 50–60 | 55 |
| Paper Debonder Concentrate | | |
| DI(hard tallow) dimethyl ammonium methylsulfate | 40–50 | 45 |
| TMPD | 20–30 | 25 |
| TMPD × 3-mole ethoxylate | 20–30 | 25 |
| Water | 2.5–10 | 5 |
| Textile Softener Concentrate (cold water dispersible, nonflammable) | | |
| Methyl-1-tallow amidoethyl-2-tallow imidazolinium methylsulfate | 50–75 | 70 |
| TMPD | 10–15 | 14 |
| TMPD × 3-mole ethoxyate | 10–15 | 12 |
| Water | 2–10 | 4 |

-continued

EXAMPLES

| Component | Typical Amount wt. % | Exemplary Amount (wt. %) |
|---|---|---|
| Oil Field Foam Booster | | |
| Blend of anionic and nonionic surfactants | 30–50 | 40 |
| Alpha-olefin sulfonate | 30–50 | 40 |
| 2-ethylhexane-1,3-diol-monoethoxylate | 10–30 | 20 |
| Oil Slick Dispersant | | |
| Nonyl phenol ethoxylate | 10–30 | 20 |
| Dioctyl sulfosuccinate | 10–20 | 15 |
| TMPD × 2-mole ethoxylate | 5–15 | 10 |
| Water | 50–60 | 55 |
| Low Foaming Automatic Dishwasher Rinse Aid | | |
| Poly(ethoxy)-poly(propoxy)block copolymer | 15–35 | 25 |
| TMPD × 7-mole ethoxylate | 15–30 | 25 |
| Water | 35–70 | 50 |

What is claimed is:

1. A stable monophasic liquid composition characterized by the ability to solubilize increased amounts of surfactant into said composition while retaining a monophasic state, which composition is useful as a dispersant of hydrophobic material and consists essentially of water; one or more surfactants selected from the group consisting of cationic surfactants, anionic surfactants, amphoteric surfactants, nonionic surfactants, and mixtures thereof;
wherein said one or more nonionic surfactants are selected from the group consisting of:
  (i) esters, amides and alkanolamides containing 6 to 40 carbon atoms, optionally 0 to 3 carbon-carbon double bonds, and optionally substituted with 1 to 20 hydroxyl groups,
  (ii) homopolymers, random copolymers and block copolymers of ethylene oxide and/or propylene oxide and/or ethylene glycol and/or propylene glycol, containing 2 to 200 repeating units,
  (iii) homopolymers, random copolymers and block copolymers of group (ii) substituted with an ester, amide, amine, alkanolamide, phenyl or phenyl-alkyl group containing up to 40 carbon atoms, and
  (iv) polysorbate –20, –32, –40, –60, –61, –69, –80, –81 and –85; and
one or more coupling agents selected from the group consisting of alkoxylates of straight, branched and cyclic alkane diols containing 7 to 12 carbon atoms, said alkoxylates containing up to 20 alkoxy units each of which is ethoxy, propoxy or butoxy, and mixtures thereof, in an amount of said one more coupling agents effective to increase the amount of said one or more surfactants that can be solubilized in said monophasic composition.

2. A composition in accordance with claim 1 wherein each of said alkoxy units is ethoxy.

3. A composition in accordance with claim 1 comprising one or more coupling agents selected from the group consisting of alkoxylates of 2,2,4-trimethyl pentane-1,3-diol and 2-ethylhexyl-1,3-diol and mixtures thereof, said alkoxylates containing up to 20 alkoxy units each of which is ethoxy, propoxy or butoxy, and mixtures thereof.

4. A composition in accordance with claim 3 wherein each of said alkoxy units is ethoxy.

5. A composition in accordance with claim 1 comprising 0.1 wt. % to 50 wt. % of said one or more coupling agents.

6. A process for solubilizing into water one or more surfactants selected from the group consisting of anionic surfactants, amphoteric surfactants, cationic surfactants, nonionic surfactants and mixtures thereof, wherein said one or more nonionic surfactants are selected from the group consisting of:
  (i) esters, amides and alkanolamides containing 6 to 40 carbon atoms, optionally 0 to 3 carbon-carbon double bonds, and optionally substituted with 1 to 20 hydroxyl groups,
  (ii) homopolymers, random copolymers and block copolymers of ethylene oxide and/or propylene oxide and/or ethylene glycol and/or propylene glycol, containing 2 to 200 repeating units,
  (iii) homopolymers, random copolymers and block copolymers of group (ii) substituted with an ester, amide, amine, alkanolamide, phenyl or phenyl-alkyl group containing up to 40 carbon atoms, and
  (iv) polysorbate –20, –32, –40, –60, –61, –69, –80, –81 and –85;
comprising combining into one monophasic composition water, said one or more surfactant, and one or more coupling agents selected from the group consisting of alkoxylates of straight, branched and cyclic, saturated, alkane diols containing 7 to 12 carbon atoms, said alkoxylates containing up to 20 alkoxy units each of which is ethoxy, propoxy or butoxy, in an amount of said one or more coupling agents effective to increase the amount of said one or more surfactants that can be solubilized in said composition.

7. A process in accordance with claim 6 wherein each of said alkoxy units is ethoxy.

8. A process in accordance with claim 6 comprising at least one alkoxylate of one or both of 2,2,4-trimethylpentane-1,3-diol and 2-ethylhexyl-1,3-diol with up to 20 alkoxy units each of which is ethoxy, propoxy or butoxy.

9. A process in accordance with claim 8 wherein each of said alkoxy units in said alkoxylate is ethoxy.

10. A process in accordance with claim 6 wherein said one or more coupling agents comprises 0.1 wt. % to 50 wt. % of said monophasic composition.

* * * * *